(12) United States Patent
Rotem et al.

(10) Patent No.: US 8,029,253 B2
(45) Date of Patent: Oct. 4, 2011

(54) FINGER-TYPE PERISTALTIC PUMP

(75) Inventors: Shachar Rotem, Hefer (IL); Uri Goldor, Givat Ada (IL)

(73) Assignee: Q-Core Medical Ltd., Petach Tikva (IL)

( * ) Notice: Subject to any disclaimer, the term of this patent is extended or adjusted under 35 U.S.C. 154(b) by 1092 days.

(21) Appl. No.: 11/791,599

(22) PCT Filed: Nov. 24, 2005

(86) PCT No.: PCT/IL2005/001249
§ 371 (c)(1), (2), (4) Date: May 24, 2007

(87) PCT Pub. No.: WO2006/056986
PCT Pub. Date: Jun. 1, 2006

(65) Prior Publication Data
US 2007/0269324 A1    Nov. 22, 2007

(30) Foreign Application Priority Data
Nov. 24, 2004    (IL) .......................................... 165365

(51) Int. Cl.
*F04B 43/12* (2006.01)
(52) U.S. Cl. ......... 417/478; 417/479; 604/151; 604/153
(58) Field of Classification Search ................. 417/474, 417/478, 479, 477.2; 604/151, 153
See application file for complete search history.

(56) References Cited

U.S. PATENT DOCUMENTS

| | | |
|---|---|---|
| 2,056,322 A | 10/1936 | Hoppe |
| 2,743,898 A | 5/1956 | King |
| 3,443,585 A | 5/1969 | Reinicke |
| 3,982,722 A | 9/1976 | Bernard |
| 3,982,725 A | 9/1976 | Clark |
| 4,014,318 A | 3/1977 | Dockum et al. |
| 4,039,269 A | 8/1977 | Pickering |
| 4,155,362 A | 5/1979 | Jess |
| 4,236,880 A | 12/1980 | Archibald et al. |

(Continued)

FOREIGN PATENT DOCUMENTS

DE    10118086 A    7/2002

(Continued)

OTHER PUBLICATIONS

Honeywell Sensing and Control, "FSS1500NSB force sensor", Golden Valley, Minnesota, USA, 1998-2004 http://sccatalog.honeywell.com/imc/printfriendly.asp?FAM=force&PN=FSS1500NSB.

(Continued)

*Primary Examiner* — Charles Freay
*Assistant Examiner* — Patrick Hamo
(74) *Attorney, Agent, or Firm* — D. Kligler I.P. Services Ltd

(57) ABSTRACT

The invention provides a finger-type peristaltic pump (2) having a body (4) and a housing (6). The body contains two or more finger-type valves (16) and a processor (22) configured to operate the valves according to a predetermined temporo-spatial pattern. The housing has a passageway (18) configured to receive a conduit. The housing has a first position in which a conduit in the passageway is positioned adjacent to the valve fingers, and a second position in which a conduit in the passageway is not adjacent to the valve fingers. The invention also provides a housing for use in the pump of the invention.

21 Claims, 5 Drawing Sheets

U.S. PATENT DOCUMENTS

| | | | |
|---|---|---|---|
| 4,270,532 A | 6/1981 | Franetzki et al. | |
| 4,320,781 A | 3/1982 | Bouvet et al. | |
| 4,450,375 A | 5/1984 | Siegal | |
| 4,489,863 A | 12/1984 | Horchos et al. | |
| 4,682,135 A | 7/1987 | Yamakawa | |
| 4,728,265 A | 3/1988 | Cannon | |
| 4,741,736 A | 5/1988 | Brown | |
| 4,893,991 A | 1/1990 | Heminway et al. | |
| 4,978,335 A | 12/1990 | Arthur, III | |
| 5,096,385 A | 3/1992 | Georgi et al. | |
| 5,103,211 A | 4/1992 | Daoud et al. | |
| 5,152,680 A | 10/1992 | Okada | |
| 5,165,874 A * | 11/1992 | Sancoff et al. | 417/474 |
| 5,213,483 A | 5/1993 | Flaherty et al. | |
| 5,222,946 A * | 6/1993 | Kamen | 604/151 |
| 5,257,978 A | 11/1993 | Haber et al. | |
| 5,290,158 A | 3/1994 | Okada et al. | |
| 5,395,320 A | 3/1995 | Padda et al. | |
| 5,429,485 A * | 7/1995 | Dodge | 417/442 |
| 5,499,969 A * | 3/1996 | Beuchat et al. | 604/30 |
| 5,509,439 A | 4/1996 | Tantardini | |
| 5,527,295 A | 6/1996 | Wing | |
| 5,575,309 A | 11/1996 | Connell | |
| 5,577,891 A | 11/1996 | Loughnane et al. | |
| 5,593,134 A | 1/1997 | Steber et al. | |
| 5,658,252 A | 8/1997 | Johnson | |
| 5,683,233 A | 11/1997 | Moubayed et al. | |
| 5,782,805 A | 7/1998 | Meinzer et al. | |
| 5,807,322 A | 9/1998 | Lindsey et al. | |
| 5,896,076 A | 4/1999 | Van Namen | |
| 5,996,964 A | 12/1999 | Ben-Shalom | |
| 6,095,189 A | 8/2000 | Ben-Shalom | |
| 6,164,921 A | 12/2000 | Moubayed et al. | |
| 6,203,296 B1 | 3/2001 | Ray et al. | |
| 6,261,262 B1 * | 7/2001 | Briggs et al. | 604/153 |
| 6,339,410 B1 | 1/2002 | Milner et al. | |
| 6,371,732 B1 | 4/2002 | Moubayed et al. | |
| 6,450,773 B1 | 9/2002 | Lipton | |
| 6,537,244 B2 | 3/2003 | Paukovits et al. | |
| 6,692,241 B2 | 2/2004 | Watanabe et al. | |
| 6,733,476 B2 | 5/2004 | Christenson et al. | |
| 7,018,361 B2 | 3/2006 | Gillespie, Jr. et al. | |
| 7,022,075 B2 | 4/2006 | Grunwald et al. | |
| 7,122,026 B2 | 10/2006 | Rogers et al. | |
| 7,163,385 B2 | 1/2007 | Gharib et al. | |
| 2002/0156402 A1 | 10/2002 | Woog et al. | |
| 2002/0165503 A1 | 11/2002 | Morris et al. | |
| 2003/0040700 A1 | 2/2003 | Hickle et al. | |
| 2003/0182586 A1 | 9/2003 | Numano | |
| 2004/0181314 A1 | 9/2004 | Zaleski | |
| 2004/0191112 A1 | 9/2004 | Hill et al. | |
| 2005/0088409 A1 | 4/2005 | Van Berkel | |
| 2006/0051218 A1 | 3/2006 | Harttig | |
| 2008/0095649 A1 | 4/2008 | Ben-Shalom et al. | |

FOREIGN PATENT DOCUMENTS

| | | |
|---|---|---|
| EP | 0215249 A1 | 3/1987 |
| EP | 0225158 A2 | 6/1987 |
| FR | 2632529 | 12/1989 |
| FR | 2753236 | 3/1998 |
| JP | 60043188 A | 3/1985 |
| JP | 6-169992 A | 6/1994 |
| JP | 2002-57738 A | 2/2002 |
| JP | 2004141418 A | 5/2004 |
| WO | 9116933 A1 | 11/1991 |
| WO | 03027503 A | 4/2003 |
| WO | 2008130644 A1 | 10/2008 |

OTHER PUBLICATIONS

U.S. Appl. No. 10/535,103 Official Action dated Feb. 2, 2009.
International Application PCT/IL2007/001398 Search Report dated Jun. 11, 2008.
International Application PCT/IL2007/001398 Patentability Report dated May 28, 2009.
International Application PCT/IL2007/001399 Search Report dated Jun. 4, 2008.
International Application PCT/IL2007/001399 Patentability Report dated May 19, 2009.
International Application PCT/IL2007/001400 Search Report dated Jul. 15, 2008.
International Application PCT/IL2007/001400 Patentability Report dated May 28, 2009.
International Application PCT/IL2007/001401 Search Report dated Sep. 24, 2008.
International Application PCT/IL2007/001401 Patentability Report dated May 28, 2009.
International Application PCT/IL2007/001402 Search Report dated Jun. 20, 2008.
International Application PCT/IL2007/001402 Patentability Report dated May 28, 2009.
International Application PCT/IL2007/001404 Search Report dated Jul. 14, 2008.
International Application PCT/IL2007/001404 Patentability Report dated May 28, 2009.
International Application PCT/IL2007/001405 Search Report dated Jul. 21, 2008.
International Application PCT/IL2007/001405 Patentability Report dated May 28, 2009.
International Application PCT/IL2005/001249 Search Report dated Apr. 5, 2006.
U.S. Appl. No. 09/125,438 Official dated May 3, 1999.
Chinese Patent Application No. 200580045471.3 "Finger-type peristaltic pump" Official Action dated Jul. 18, 2008.
European Application No. 05810500.8 Official Action dated Jul. 6, 2009.
International Application PCT/IL1997/000289 Search report dated Jan. 27, 1998.
International Application PCT/IL1997/000290 Search Report dated Jan. 27, 1998.
International Application PCT/IL2003/000947 Search Report dated Mar. 3, 2004.
U.S. Appl. No. 09/125,438 Official dated Jul. 15, 1999.
Chinese Patent Application No. 200780041966.8 Official Action dated Jul. 13, 2010.
U.S. Appl. No. 12/514,311 Official dated Sep. 16, 2010.
U.S. Appl. No. 12/644,027 Official Action dated Apr. 28, 2011.
European Patent Application # 10192477.7 Search Report dated May 10, 2011.
U.S. Appl. No. 12/514,310 Official Action dated Jul. 21, 2011.
U.S. Appl. No. 12/463,399 Official Action dated Jul. 21, 2011.

* cited by examiner

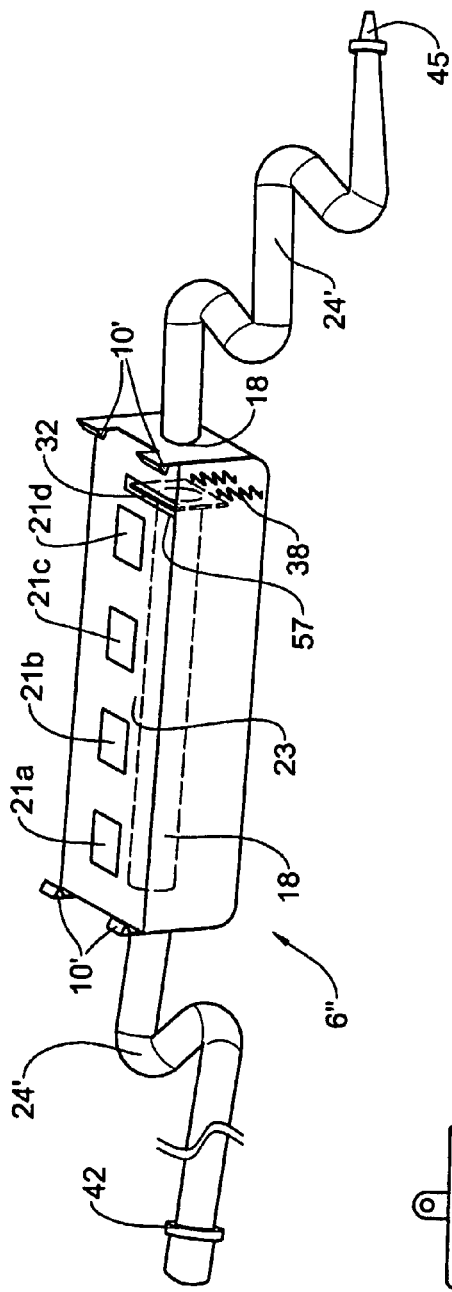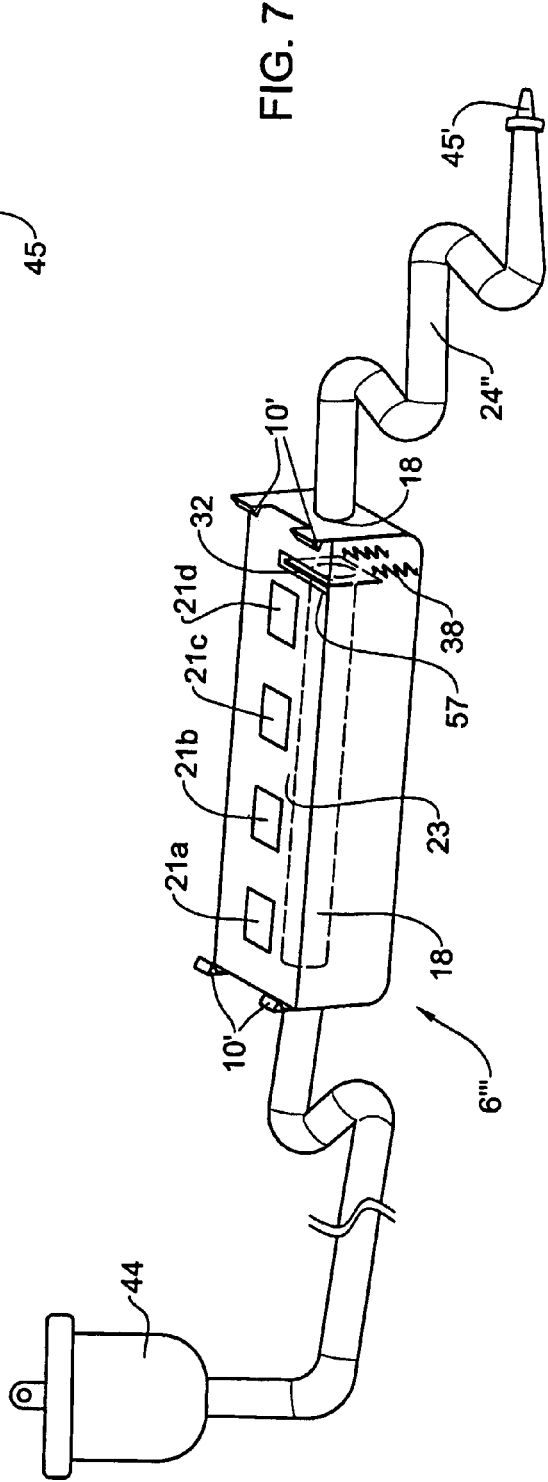

FINGER-TYPE PERISTALTIC PUMP

CROSS-REFERENCE TO RELATED APPLICATIONS

This application is based on PCT Application No. PCT/IL/2005/001249 filed Nov. 24, 2005, which claims priority from Israeli patent application No. 165365 filed Nov. 24, 2004.

FIELD OF THE INVENTION

The present invention relates to pumps and more specifically to finger-type peristaltic pumps.

BACKGROUND OF THE INVENTION

Peristaltic pumps are used for creating a flow of a fluid in an elastic tubular conduit. These pumps have many medical and industrial applications.

In one form of peristaltic pumps, a rotor is used to rotate a plurality of eccentric cams. Each cam, in turn, intermittently collapses the elastic conduit at an initial contact point, and slides along the conduit over a short distance as the rotor turns. A second cam contacts the initial contact point, and the first cam is then released from the conduit as the second cam slides along the conduit. As this process is repeated, a flow of fluid in the conduit is generated in the direction of the sliding of the cams.

In another form of peristaltic pumps referred to herein as a "finger-type peristaltic pump", a series of valves is aligned along an elastic conduit. Each valve comprises a "finger" that can alternate between two positions. In one position, the finger is extended from the valve so as to contact the conduit and to at least partially occlude the conduit at the point of contact. In the other position, the finger is retracted and does not contact the conduit. The series of valves is operated according to a temporo-spatial pattern so as to generate a flow in the conduit.

Commercially-available finger-type peristaltic pumps essentially include a hinged door, which is usually a rotatable member, adapted to continuously press the fluid conduit inserted in the body towards the valve fingers located in the body when in its closed configuration. This door is a frequent cause of failure in the pump's operation: the door is frequently opened while the pump in action, thus causing the conduit to fall out of place and cease pumping, opening the door and holding it open so as to insert the pipe requires three pairs of hands and thus can only be performed by two persons together, necessitating the presence of two medical personnel.

In addition, in this configuration the conduit pipe is exposed, i.e. is not wrapped or coated in any other material and is thus more vulnerable to contamination. The pipe is normally made of thin flexible silicon, which is worn down by the tip of the finger pump during extended use. Since it is common hospital practice to make use of a single pipe during the course of a patient's hospitalization, without replacing the pipe, during the course of use the pipe becomes increasingly vulnerable to puncturing, thus enabling contaminants (such as blood, HIV, Hepatitis virus, radioactive medicaments etc.) which may be present in the patients bloodstream or in the infusion being delivered, to accumulate on the outer surface of the pipe. If the pipe is inadvertently touched by unprotected hospital personnel, the user himself or his visitors, such contaminants may rapidly spread and be transmitted to a wider population.

The configurations currently available comprise three separate components: body, conduit and door. Inserting the conduit into the body, and then closing the door accurately requires considerable experience and manual dexterity, and can not normally be performed by chronically ill, physically limited or geriatric patients independently, thus requiring the constant attention of hospital personnel.

U.S. Pat. No. 5,395,320 to Padda et al. teaches a programmable peristaltic fingers infusion pump with an interchangeable variety of disposable tubing in commonly available sizes and types. The pump essentially comprises no less than two doors: an outer door (1) and an inner door (20), wherein the outer door (1) protects the inner door (20), which is kept in a close configuration by door latch (2).

U.S. Pat. No. 5,807,322 to Lindsey et al. presents a peristaltic pump unit that has a flexible infusion line (28) which is repeatedly compressed by a pusher (30). Line (28) is positioned in an elongated groove or channel (58) which acts to restrain sideways bulging of the line as it is being compressed by the pusher. The patent teaches that peristaltic pumps may be associated with a cassette which acts as a reservoir for the fluid to be pumped.

FR 2,753,236 to Ray et al. introduces a miniature peristaltic pump. The pump comprises inter alia a rotor, and a support piece equipped with a rounded-off portion (308) arranged in a substantially concentric manner to the rotor and against which, during operation, said rollers compress a flexible tubing (202) connected to a solution reservoir (201). Tubing (202) is inserted into circular opening (310), closed off by a cover (311). Thus again, slidable door member (311) ensures conduit (202) location directly adjacent to the pumping effecters (here rollers 110). Again the body and the door are integrally attached.

FR 2,632,529 to Gautier et al. teaches a drug injector with a removable reservoir in which the infusion liquid container may be inserted—held to control box by a pivoting arm engaged by head. The patent discloses a pump having a body (2) and rotatable pumping effecter (pump drum 7) towards which pipe (4) is pressed by means of maneuverable arm (10) being interconnected to body (2) by an hinge. Arm (10) is forcefully secured to body (2) by screw (16).

SUMMARY OF THE INVENTION

The present invention provides a finger-type peristaltic pump. The pump of the invention may be used, for example, in a medical context for infusing a liquid into the body of a subject.

The peristaltic pump of the invention comprises a housing for holding a segment of an elastic conduit adjacent to the fingers of the valves of the pump. In one embodiment, the housing is hinged at one end to the body of the pump. The housing is swung out from the body in order to introduce a segment of an elastic conduit into the housing. The housing is then swung back towards the body so as to position the conduit segment adjacent to the fingers of valves of the pump. The housing may be maintained in this closed position by a snapping mechanism, or by a latch.

In another embodiment, the housing of the invention is detachable from the body of the pump. A segment of a conduit may be introduced into the housing when the housing is detached. The housing is then attached onto the body of the pump so as to position the segment of the conduit adjacent to the valve fingers. In a most preferred embodiment, the housing is integral with a segment of a conduit. In this case, the conduit in the housing has fittings at each end allowing the conduit to be attached at each end to another piece of conduit, so that the pump may be integrated into a pumping system. In the detachable housing embodiment, the housing may be disposable.

The housing of the invention preferably includes an antifree-flow mechanism to prevent the flow of fluid in the segment of the conduit in the housing when the conduit is not adjacent to the fingers. The antifree-flow mechanism has a non-obstructing position in which the antifree-flow device does not prevent flow in the conduit, and an obstructing position in which the antifree-flow device prevents flow in the conduit. The antifree-flow device is spring biased in the obstructing position, so that when the housing is swung away or detached from the body of the pump, the antifree-flow device spontaneously assumes its obstructing position. This prevents unintentional flow in the conduit when the housing is swung out or detached from the body of the pump. The antifree-flow device preferably includes an override mechanism that allows the antifree-flow device to be temporarily latched in its non-obstructing position when the housing is swung away or detached from the body in order to allow a segment of conduit to be introduced into the housing. As the housing is brought to its position in which it is attached to the pump, the antifree-flow device is brought to its unlatched non-obstructing position, regardless of whether it was previously in its obstructing position or its latched non-obstructing position. The antifree flow device may prevent flow in the conduit in both directions or only in one direction.

Thus, in its first aspect, the invention provides a finger-type peristaltic pump comprising a body and a housing, the body containing two or more finger-type valves and a processor configured to operate the valves according to a predetermined temporo-spatial pattern, the housing having a passageway configured to receive a conduit, the housing having a first position in which a conduit in the passageway is positioned adjacent to the valve fingers, and a second position in which a conduit in the passageway is not adjacent to the valve fingers.

In its second aspect, the invention provides a housing for use in the pump of the invention.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 6 shows a housing for use in the peristaltic pump of FIG. 5 integral with a conduit; and FIG. 7 shows a housing for use in the peristaltic pump of FIG. 5 integral with a conduit and a fluid reservoir.

DETAILED DESCRIPTION OF THE INVENTION

Figure 1A:
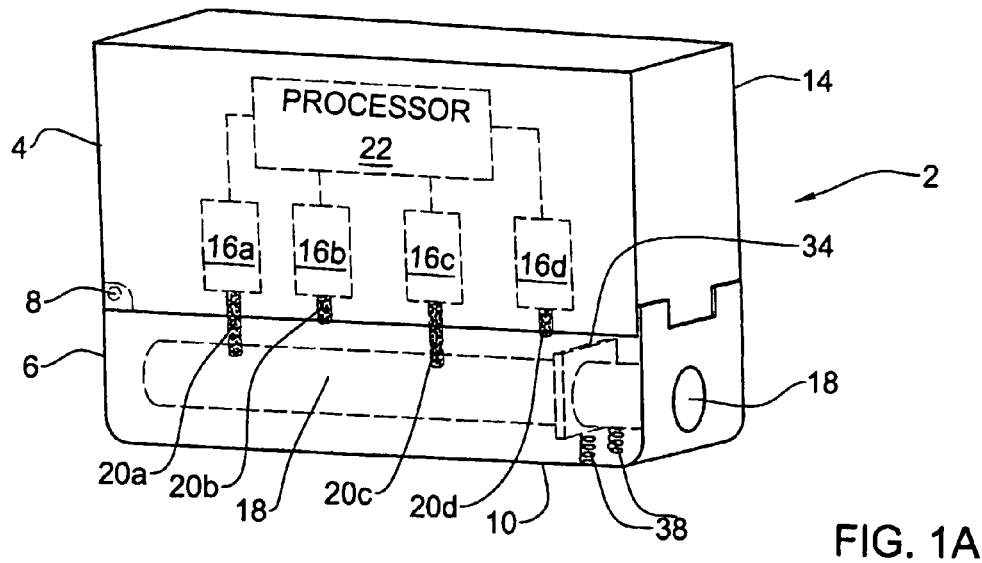
FIG. 1 shows a peristaltic pump having a housing in accordance with one embodiment of the invention.
Figure 1B:
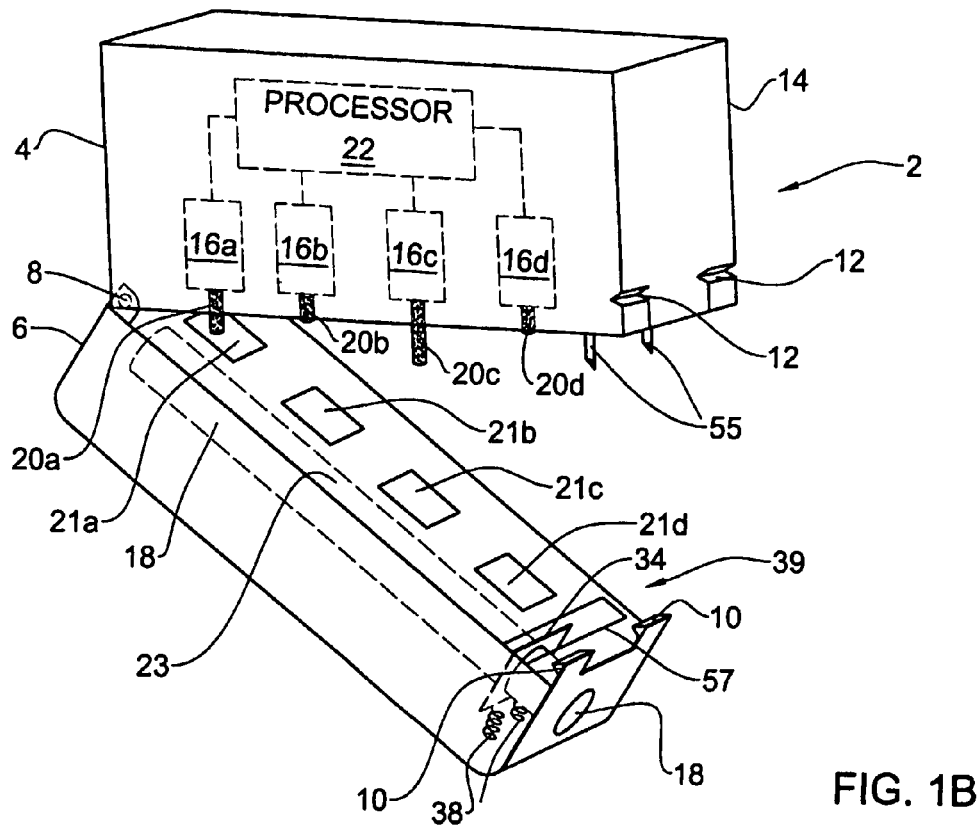

FIG. 1 shows a finger-type peristaltic pump 2 in accordance with one embodiment of the invention. The pump 2 has a body 4 and a housing 6. The housing 6 is hinged to the body 4 at a hinge 8 so as to allow the housing 6 to pivot between a closed position shown in FIG. 1a and an open position shown in FIG. 1b. The housing 6 snaps into the closed position by means of projections 10 located at the end of the housing 6 distal to the hinge 8 that snaps into mated notches 12 in the body 4.

The housing 6 has a passageway 18 dimensioned to receive a segment of an elastic conduit as explained below.

The body 4 has a housing 14 containing a plurality of electrically operated valves 16. Four valves, 16a to 16d, are shown in FIG. 1. This is by way of example only and the pump may have any number of valves 16 greater than two. Each valve 16 has a respective finger 20. Each valve 16 is electrically operable to oscillate its finger 20 from a retracted position in which the finger 20 does not contact a conduit in the passageway 18 and an extended position in which the finger 20 at least partially occludes a flexible conduit in the passageway 18. The fingers 20b and 20d are shown in FIG. 1 in their retracted position, while the fingers 20a and 20d are shown in FIG. 1 in their extended position. Each finger 20 corresponds to a finger hole 21 in the upper surface 23 of the housing 6. A finger 16, when in its extended position, extends through its respective finger hole 20 into the housing 6 to compress a region of a conduit in the passageway 18.

The body 4 also contains a processor 22 configured to operate the valves 16 according to a temporo-spatial pattern so as to generate a flow of fluid in an elastic conduit in the passageway 18 when the housing 6 is in its closed position shown in FIG. 1a, as is known in the art.

Figure 2:
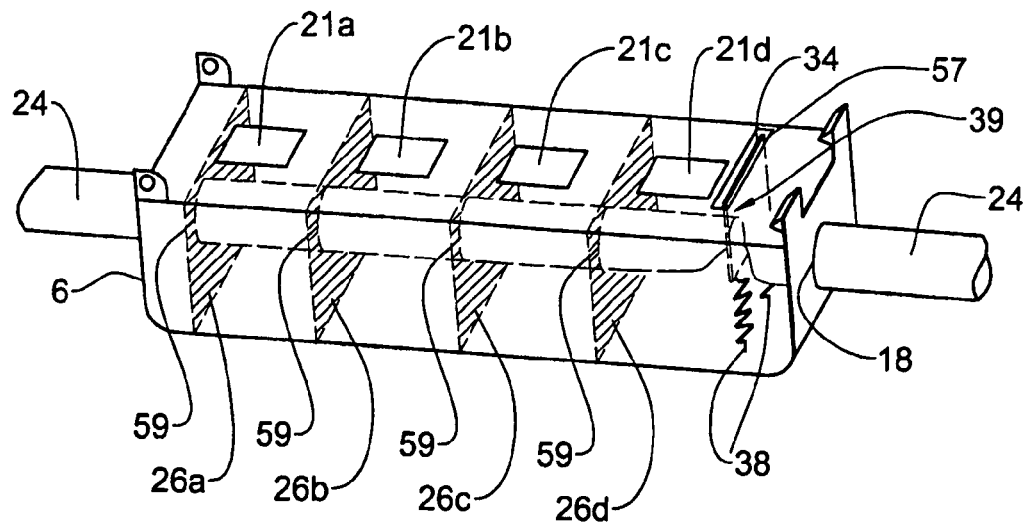
FIG. 2 shows the housing of the peristaltic pump of FIG. 1.

FIG. 2 shows the housing 6 in greater detail. A conduit 24 made from an elastic material has been introduced into the passageway 18. The conduit 24 is supported in the passage 18 by one or more supports 26 that prevent bulging of the conduit 24 between two fingers 20 in the extended state. The supports 26 also prevent lateral movement of the conduit 24 in the passageway 18 during operation of the pump. The cross sectional shape of the passageway 18 is determined by the shape of holes 59 in the supports 26

Figure 3:
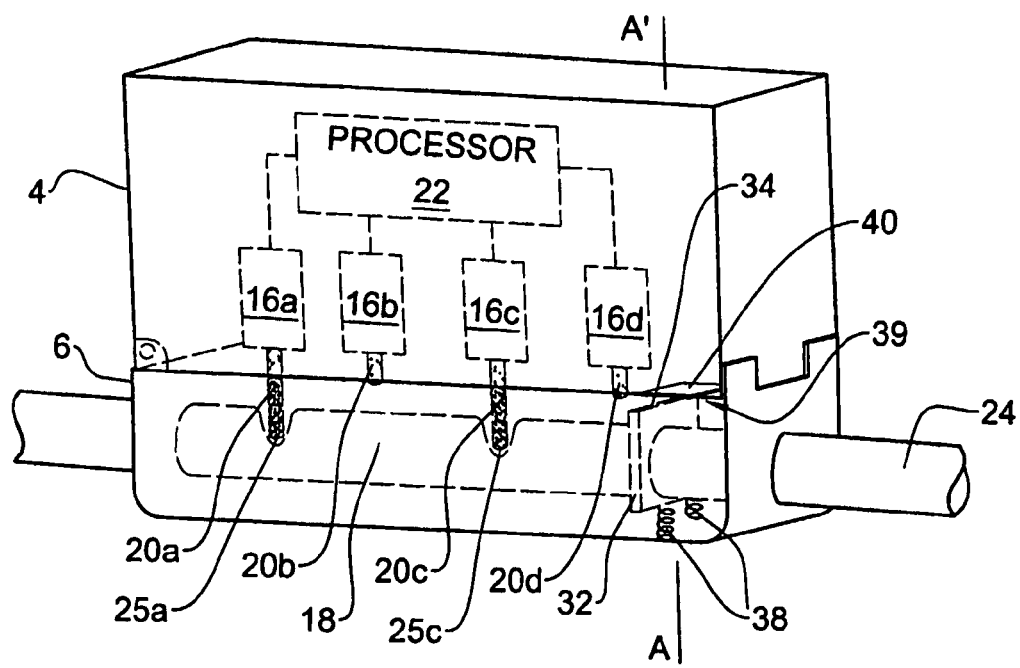
FIG. 3 shows the peristaltic pump of FIG. 1 together with a conduit.

FIG. 3 shows the pump 2 with a conduit 24 in the passageway 18 in its closed position shown also in FIG. 1a. As can be seen, the fingers 20a and 20c are in their extended position and therefore constrict the conduit 24 and the points of contact 25a and 25c. As explained above, the valves 16 are operated by the processor 22 so that the fingers 20 alternate between their retracted and extended positions so as to generate a flow in the conduit 24

Figure 4A:
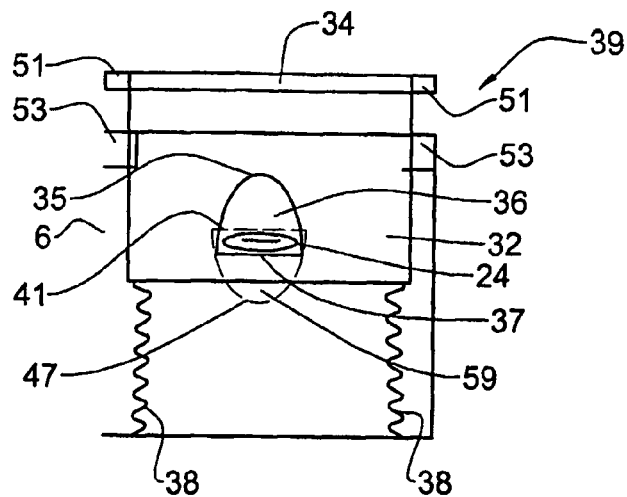
FIG. 4 shows an anti free flow device for use in the housing of FIG. 3.
Figure 4B:
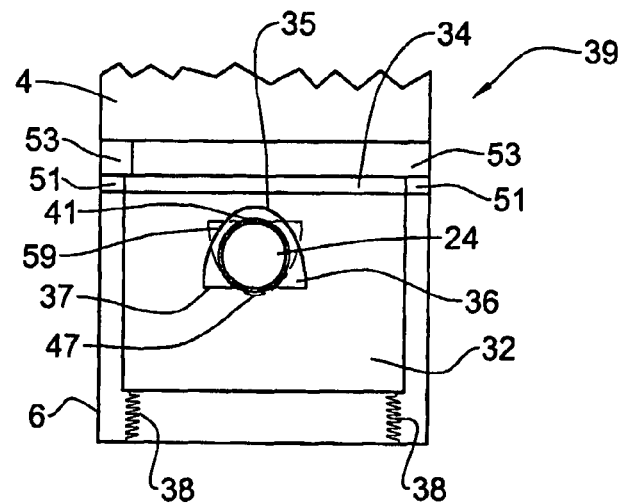
Figure 4C:
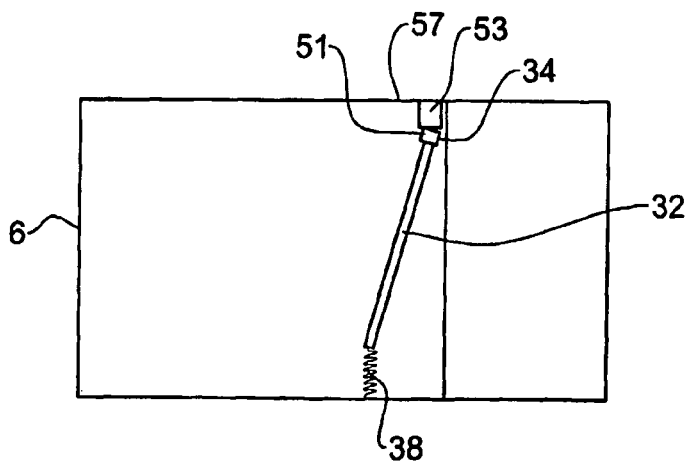

The housing 6 includes an anti-free flow mechanism 39. The anti-free flow mechanism prevents the flow of fluid in the conduit 24 when the housing 6 is not in its closed position shown in FIG. 1a. The anti-free flow mechanism is shown in FIG. 4 in a cross section AA' of the pump 2 shown in FIG. 3. The housing 6 is shown in its open position in FIG. 4a and in its closed position in FIG. 4b. The anti-free flow includes an occlusion plate 32, from which an actuating tab 34 extends (see also FIGS. 1 and 2). The occluding plate 32 has a D-shaped hole 36 having a straight bottom edge 37 and an upper arcuate edge 35. A hole 59 of the passageway 18 is indicated in FIG. 4 by a broken line. The holes 59 of the passageway 18 are "D" shaped, having a straight upper edge 41 and an arcuate lower edge 47. The occluding plate is slidable from an obstructing position shown in FIG. 4a and a non-obstructing position shown in FIG. 4b. The occluding plate 32 is spring biased in its obstructing position by means of springs 38. In its non-obstructing position (FIG. 4b), the hole 36 of the occlusion plate 32 is essentially aligned with the passageway 18 so that the conduit 24 is unobstructed. In its obstructing position (FIG. 4a), the hole 36 and the passageway 18 only partially overlap, so that the conduit 24 is collapsed between the straight edge 37 of the hole 36 and the straight edge 41 of the passageway 18. The conduit 24 is thus obstructed, as shown in FIG. 4a. This prevents unintentional flow of fluid in the conduit 24 when the housing 6 is swung out from the body 4.

When the housing 6 is swung out from the body 4, the obstructing plate 32 may be brought into its non-obstructing position (FIG. 4b) by manually depressing the tab 34. The tab 34 may be temporarily latched with the plate 32 in its non-obstructing position. This may be done for example, when it is desired to allow free flow of fluid in the conduit. The plate 32 in its latched non-obstructing position is shown in a side view in FIG. 4c. Extensions 51 on either side of the tab 34 (see also FIGS. 4a and 4b) are lodged under extensions 53 of the inner wall of the housing 6. The obstructing plate 32 is brought into its latched non-obstructing position (FIG. 4a) from its unlatched non-obstructing position (FIG. 4b) by rotating the plate 32 so as to lodge the extensions 51 under the extensions 53. An upwards pressure on the plate 32 by the springs 38 presses the extensions 51 onto the extensions 53 so as to maintain the anti-free-flow mechanism in its latched non-obstructing state. The obstructing plate 32 may be manually released from its lodged, non-obstructing position by rotating the plate 32 back so as to dislodge the extensions 51 from under the extensions 53. The plate 32 then passes through a slot 57 in the housing 6 in order to regain its obstructing position (FIG. 4a) under the influence of the spring 38. The housing 6 is then swung shut onto the body 4 (FIG. 4b). If the anti-free flow mechanism is in its latched non-obstructing position when the housing is swung onto the body 4, a pair of wedges 55 extending from the body 4 (FIG. 1b) rotate the plate 32 as the housing 6 is being swung shut so as to dislodge the extensions 51 from under the extensions 53. A static plate 40 fixed in the body 4 depresses the tab 34 against the spring 38 so to maintain the plate 32 in its unlatched non-obstructing position when the housing 6 is in its closed position.

Figure 5A:
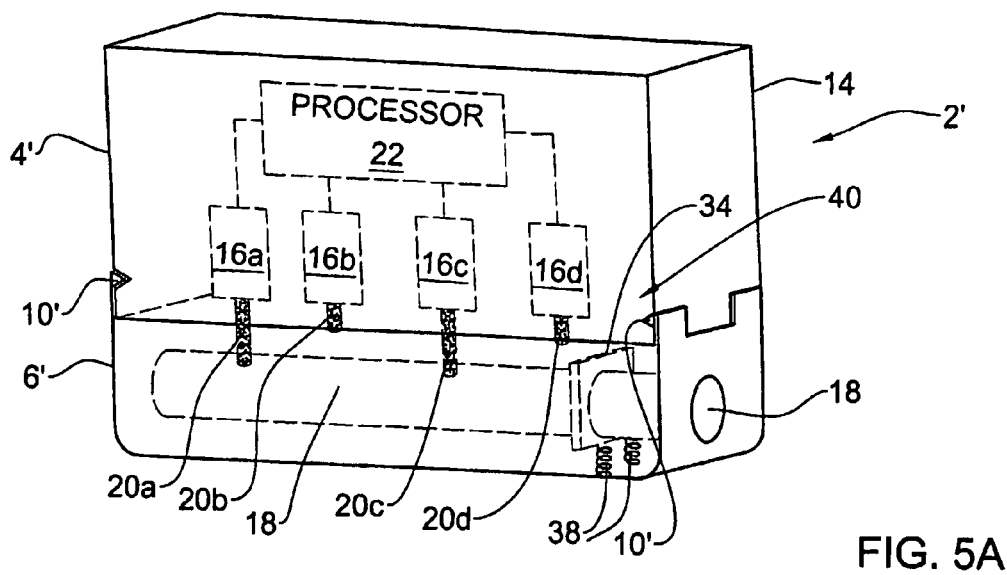
FIG. 5 shows a peristaltic pump having a housing in accordance with another embodiment of the invention.
Figure 5B:
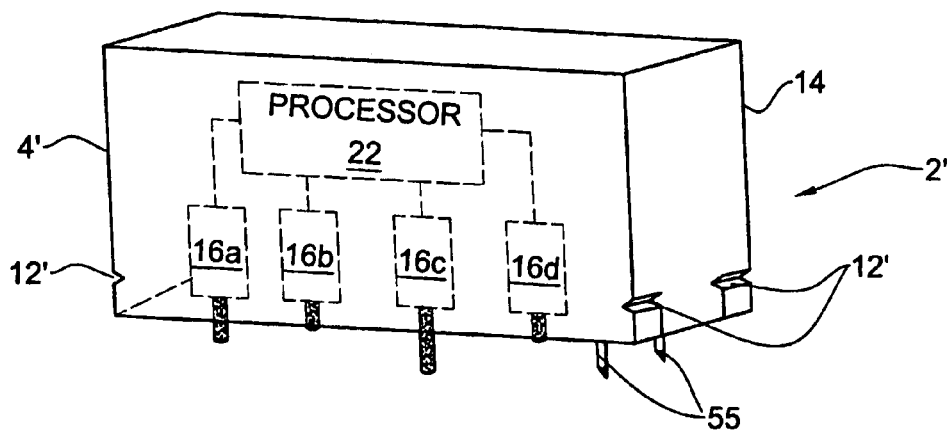
Figure 5B:
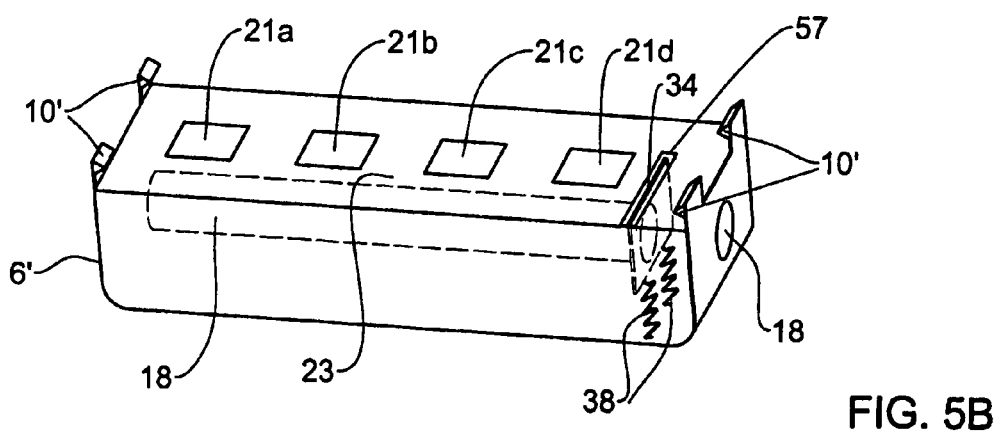

FIG. 5 shows a finger-type peristaltic pump 2' in accordance with another embodiment of the invention. Components of the pump 2' similar to components of the pump 2 are designated by the same reference numerals without further comment. The pump 2' has a body 4' and a housing 6'. The housing 6' is reversibly attachable to the body 4' by means of projections 10' located at both ends of the housing 6' that snap into mated notches 12' on opposite sides of the body 4'. In FIG. 5a, the housing 6' is shown attached to the body 4', and in FIG. 5b, the housing 6' is shown detached from the body 4'. The pump 2' is operated as described above in reference to the pump 2. The housing 6' may be disposable.

FIG. 6 shows a housing 6" that may be used with the body 4' instead of the housing 6'. Components of the housing 6" similar to components of the housing 6' are designated by the same reference numerals without further comment. The housing 6" is integral with an elastic conduit 24'. The conduit 24' is provided at one end with a connector 42 suitable for forming a fluid connection with an upstream fluid reservoir, such as an infusion bag (not shown). The other end of the conduit 24' is provided with a connector 45 for forming a fluid connection with a downstream device, such as a needle (not shown).

FIG. 7 shows a housing 6'" that may be used with the body 4' instead of the housing 6'. Components of the housing 6" similar to components of the housing 6' are designated by the same reference numerals without further comment. The housing 6" is integral with an elastic conduit 24". The conduit 24" is integral with an upstream fluid reservoir, such as an infusion bag 44. The other end of the conduit 24" is provided with a connector 45' for forming a fluid connection with a downstream device, such as a needle (not shown).

The invention claimed is:

1. A finger-type peristaltic pump comprising:
   a body, which contains two or more fingers having an extended position and a retracted position; and
   a housing comprising a passageway having a first hole configured to receive a conduit so that the fingers, when in their extended position, extend into the housing to compress a segment of the conduit in the passageway,
   wherein the housing comprises an anti-free flow mechanism to prevent a flow of fluid in the segment of the conduit in the passageway when the conduit is not adjacent to the fingers, the anti-free flow mechanism comprising an occluding plate, which has a second hole located adjacent to the first hole, and which is slidable between a non-obstructing position, in which the first and second holes are aligned to permit the flow of fluid in the segment, and an obstructing position, in which the conduit is collapsed between respective edges of the first and second holes,
   wherein the anti-free flow mechanism has an obstructing state, an unlatched non-obstructing state and a latched non-obstructing state, and
   wherein closing the housing against the body when the anti-free flow mechanism is in the latched non-obstructing state causes the anti-free flow mechanism to transition to the unlatched non-obstructing state.

2. The pump according to claim 1, wherein said housing is completely detachable from said body of the pump, enabling two configurations (i) attached to said body or (ii) completely detached and carried separately.

3. The pump according to claim 2 wherein the housing is hinged to the body and swings around a hinge between the first configuration and the second configuration.

4. The pump according to claim 3 wherein the housing is disposable.

5. The pump according to claim 1, wherein the housing comprises supports preventing bulging of the conduit in the passageway.

6. The pump according to claim 5, wherein said supports prevent lateral movement of the conduit in the passageway during operation of the pump.

7. The pump according to claim 1, wherein the anti-free flow mechanism is configured to prevent flow in two directions in the conduit when the anti-free flow mechanism is in an obstructing state.

8. The pump according to claim 1, wherein the anti-free flow mechanism is configured to prevent flow in one direction in the conduit when the anti-free flow mechanism is in an obstructing state.

9. The pump according to claim 1, wherein the housing is disposable.

10. The pump according to claim 1, wherein the housing is integral with the conduit.

11. The pump according to claim 1, wherein the conduit is provided at an end with a connector for forming a fluid connection with a fluid reservoir.

12. The pump according to claim 11 wherein the fluid reservoir is an infusion bag.

13. The pump according to claim 1, wherein the housing is provided at an end with a connector for forming a fluid connection with a downstream device.

14. The pump according to claim 13 wherein the downstream device is a needle.

15. The pump according to claim 1, wherein the conduit is integral with a fluid reservoir.

16. The pump according to claim 15 wherein the fluid reservoir is an infusion bag.

17. The pump according to claim 15 wherein the conduit is provided at an end with a connector for forming a fluid connection with a downstream device.

18. The pump according to claim 17 wherein the downstream device is a needle.

19. The pump according to claim 1, wherein the first and second holes are D-shaped, having respective straight edges on opposing sides of the conduit, such that in the obstructing position the conduit is collapsed between the respective straight edges.

20. A finger-type peristaltic pump comprising:
- a body, which contains two or more fingers having an extended position and a retracted position; and
- a housing comprising a passageway having a first hole configured to receive a conduit so that the fingers, when in their extended position, extend into the housing to compress a segment of the conduit in the passageway,
- wherein the housing comprises an anti-free flow mechanism to prevent a flow of fluid in the segment of the conduit in the passageway when the conduit is not adjacent to the fingers, the anti-free flow mechanism comprising an occluding plate, which has a second hole located adjacent to the first hole, and which is slidable between a non-obstructing position, in which the first and second holes are aligned to permit the flow of fluid in the segment, and an obstructing position, in which the conduit is collapsed between respective edges of the first and second holes,
- wherein the anti-free flow mechanism comprises a spring, which biases the occluding plate in the obstructing position, and wherein the body comprises a static plate, which depresses the spring when the housing is closed against the body so as to maintain the occluding plate in the non-obstructing position.

21. The pump according to claim 20, wherein the anti-free flow mechanism has an obstructing state, an unlatched non-obstructing state and a latched non-obstructing state.

* * * * *